United States Patent
Lu et al.

(10) Patent No.: US 11,457,850 B2
(45) Date of Patent: Oct. 4, 2022

(54) NEURAL-SIGNAL AMPLIFIER AND MULTI-CHANNEL NEURAL-SIGNAL AMPLIFYING SYSTEM

(71) Applicant: National Chiao Tung University, Hsinchu (TW)

(72) Inventors: Hung-Pin Lu, Hsinchu (TW); Po-Tsang Huang, Hsinchu (TW); Wei Hwang, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 313 days.

(21) Appl. No.: 16/704,408

(22) Filed: Dec. 5, 2019

(65) Prior Publication Data
US 2020/0178823 A1    Jun. 11, 2020

(30) Foreign Application Priority Data
Dec. 5, 2018 (TW) .................. 107143556

(51) Int. Cl.
| | |
|---|---|
| *H03F 1/30* | (2006.01) |
| *H03F 3/45* | (2006.01) |
| *A61B 5/24* | (2021.01) |
| *A61B 5/00* | (2006.01) |
| *A61B 5/31* | (2021.01) |

(52) U.S. Cl.
CPC .................. *A61B 5/24* (2021.01); *A61B 5/31* (2021.01); *A61B 5/4064* (2013.01); *H03F 1/303* (2013.01); *H03F 3/45475* (2013.01); *H03F 2203/45551* (2013.01)

(58) Field of Classification Search
CPC ...... H03F 1/303; H03F 3/005; H03F 3/45475; H03F 2203/45551; H03F 3/45183; H03F 3/45192; H03F 2203/45514; H03F 3/45632; A61B 5/24; A61B 5/31; A61B 5/4064; A61B 5/30; A61B 5/369; A61B 5/7225
USPC ............... 330/9, 252–261; 327/307; 600/544
See application file for complete search history.

(56) References Cited

U.S. PATENT DOCUMENTS

| | | | |
|---|---|---|---|
| 5,420,550 A | 5/1995 | May | |
| 5,914,638 A * | 6/1999 | He | G11C 27/026 330/258 |
| 6,778,009 B1 * | 8/2004 | Lee | H03F 3/005 327/124 |

(Continued)

FOREIGN PATENT DOCUMENTS

| | | |
|---|---|---|
| WO | WO2008011370 A2 | 1/2008 |
| WO | WO2009141457 A1 | 11/2009 |
| WO | WO2012177654 A2 | 12/2012 |

*Primary Examiner* — Hieu P Nguyen
(74) *Attorney, Agent, or Firm* — Muncy, Geissler, Olds & Lowe, P.C.

(57) ABSTRACT

A neural-signal amplifier includes an amplifier, a switched-capacitor circuit-input unit, a switched-capacitor feedback-circuit unit, and a switched-capacitor circuit-output unit. Each of the switched-capacitor circuit-input unit, the switched-capacitor feedback-circuit unit, and the switched-capacitor circuit-output unit includes a plurality of differential switches, a plurality of common mode switches, and a plurality of capacitors. By controlling the switches to turn on or performing the switched-capacitor operation, the neural-signal amplifier is controlled to suppress the DC drift and reconstruct the DC input of the common-mode power supply.

8 Claims, 13 Drawing Sheets

(56) References Cited

U.S. PATENT DOCUMENTS 7,724,063 B1    5/2010  Chang et al.
2010/0106041 A1*  4/2010  Ghovanloo .......... A61B 5/0006
                                                600/544

* cited by examiner

NEURAL-SIGNAL AMPLIFIER AND MULTI-CHANNEL NEURAL-SIGNAL AMPLIFYING SYSTEM

CROSS-REFERENCE TO RELATED APPLICATION

This application claims priority from Taiwan Patent Application No. 107143556, filed on Dec. 5, 2018, in the Taiwan Intellectual Property Office, the content of which is hereby incorporated by reference in its entirety for all purposes.

BACKGROUND OF THE INVENTION

1. Field of the Invention

The present invention relates to a neural-signal amplifier, more particularly to a fully-integrated neural-signal amplifier.

2. Description of the Related Art

It can be said that human behavior is completely controlled by a brain, and abnormality of brain physiology often causes disorder in cognition and behavior, as the cognition and behavior are interrelated with each other. In recent years, brain science research has caused a sensation around the world, and the growing trend has been equipped with multidisciplinary integration and influence. The research of brain science has developed a cognitive science which further analyzes human behavior by exploring the cognitive function of a brain, as well as a brain physiology which provides solutions for tackling with brain diseases by investigating the structure and mechanism of brain cells and neural systems.

However, there are requirements for these high demands for the research of brain physiology. A magnetoencelphalographic scan (MEG) with high sensitivity is often used as a detecting equipment. Moreover, several research institutes utilize a magnetoencelphalographic scan to perform human brain mapping in order to detect sophisticated changes in brain waves for the analysis of brain science.

For the purpose of precisely mapping out the human brain spectrum and exploring the signal transmission of cranial nerves, neural-imaging technology with high spatial and temporal resolution is therefore required. Wherein, the measurement of the micro-cerebral cortex signals with ultra-high resolution refers to placing a high-density electrode array on the surface of the cerebral cortex to measure the electric-potential activity of neurons in the cerebral cortex and electric-potential changes on the surface of the cerebral cortex. Hence, in order to improve the precision of electro-physiological signal resolution, it is essential to develop the retrieval technology of micro-electrocorticography (micro-ECoG or uECoG).

For the technology in the past, external DC shielding capacitors are adopted for the detecting neural-signal circuit design to suppress DC drift of the neural signal. Please refer to FIG. 1, which depicts a conventional neural-signal detecting circuit. As shown, the conventional technique can achieve the effect of suppressing the drift of neural signals through the shielding capacitors. Nevertheless, in the circuit architecture of the conventional technique, a capacitor with larger capacitance is required to shield the detecting neural-signal circuit and to amplify the signal, thus resulting in the overall detecting neural-signal circuit being over-sized.

Changes in the surface of the cerebral cortex are complicated and retrieving a micro-electrocorticographic scan (micro-ECoG or uECoG) requires a high-density electrode array. If the neural-signal detecting circuit is over-sized, the number of channels of the electrode array and the physiological signal detecting range to which the measuring device is applied will be limited. Furthermore, when integrating a multi-channel neural-signal acquisition system, additional burden on the overall system will occur. This would not only create difficulty integrating system design, but also affect measurement accuracy.

SUMMARY OF THE INVENTION

According to the purpose, the present invention provides a neural-signal amplifier including an amplifier, a switched-capacitor circuit-input unit, a switched-capacitor feedback-circuit unit, and a switched-capacitor circuit-output unit. The amplifier includes a first input terminal, a second input terminal, a first output terminal, a second output terminal, and a common-mode feedback-input terminal. The first input terminal receives a first input signal, the second input terminal receives a second input signal, and the common-mode feedback-input terminal receives a common-mode feedback-input signal to generate and respectively output a first amplified output signal and a second amplified output signal from the first output terminal and the second output terminal. The switched-capacitor circuit-input unit receives a first bio-potential signal and a second bio-potential signal to generate the first input signal and the second input signal. Two switched-capacitor feedback-circuit units are respectively electrically connected between the first input terminal and the first output terminal of the amplifier and between the second input terminal and the second output terminal. The switched-capacitor circuit-output unit receives the first amplified output signal and the second amplified output signal to generate the common-mode feedback-input signal. Each of the switched-capacitor circuit-input unit, the two switched-capacitor feedback-circuit units, and the switched-capacitor circuit-output unit is further provided with a plurality of differential switches and a plurality of common-mode switches. When the plurality of differential switches are turned on and the plurality of common-mode switches are turned off, the neural-signal amplifier is in a differential amplifying state. When the plurality of differential switches are turned off and the plurality of common-mode switches are turned on, the neural-signal amplifier is in a common-mode reconstructing state. The neural-signal amplifier can be switched between the differential amplifying state and the common-mode reconstructing state by operating the plurality of differential switches and the plurality of common-mode switches in order to reconstruct a common-mode current to suppress DC current drift.

Preferably, the switched-capacitor circuit-input unit includes a first differential switch connected to a first bio-potential signal source which generates the first bio-potential signal; a first common-mode switch connected between the first differential switch and a first capacitor, and the first capacitor connected to the first input terminal; a second differential switch connected to a second bio-potential signal source which generates the second bio-potential signal; a second common-mode switch connected between the second differential switch and a second capacitor, and the second capacitor connected to the second input terminal; and a first reference voltage connected between the first common-mode switch and the second common-mode switch.

Preferably, the switched-capacitor feedback-circuit unit includes a third common-mode switch; a fourth common-mode switch connected to a fifth bias source which supplies a fifth bias, and the fifth bias source further connected to the third common-mode switch; a third differential switch connected to the fourth common-mode switch; a third capacitor connected between the third common-mode switch and the fourth common-mode switch; and a low-pass capacitor connected between the third common-mode switch and the third differential switch. The third capacitor, the low-pass capacitor, and the third common-mode switch are connected to the first input terminal or the second input terminal, and the low-pass capacitor and the fourth common-mode switch are respectively connected to the first output terminal and the second output terminal.

Preferably, the switched-capacitor circuit-output unit includes a sixth common-mode switch connected to the first output terminal; a seventh common-mode switch connected to the common-mode feedback-input terminal; an eighth common-mode switch connected to the second output terminal; a sixth differential switch, one terminal thereof connected to the sixth common-mode switch and another terminal thereof connected to a fifth bias source which supplies a fifth bias; a seventh differential switch, one terminal thereof connected to the seventh common-mode switch and another terminal thereof connected to a first bias source which supplies a first bias; an eighth differential switch, one terminal thereof connected to the eighth common-mode switch and another terminal thereof connected to the fifth bias source which supplies the fifth bias; a fifth capacitor, one terminal of the fifth capacitor connected between the first output terminal and the seventh common-mode switch, and another terminal of the fifth capacitor connected between the common-mode feedback-input terminal and the seventh differential switch; a sixth capacitor, one terminal of the sixth capacitor connected between the common-mode feedback-input terminal and the seventh common-mode switch, and another terminal of the sixth capacitor connected between the second output terminal and the eighth common-mode switch; a seventh capacitor, one terminal of the seventh capacitor connected between the sixth common-mode switch and the eighth differential switch, and another terminal of the seventh capacitor connected between the seventh common-mode switch and the seventh differential switch; and an eighth capacitor, one terminal of the eighth capacitor connected between the seventh common-mode switch and the seventh differential switch, and another terminal of the eighth capacitor connected between the eighth common-mode switch and the eighth differential switch.

Preferably, the neural-signal amplifier further includes a switch-control unit electrically connected to the switched-capacitor circuit-input unit, the two switched-capacitor feedback-circuit units, and the switched-capacitor circuit-output unit. The switch-control unit outputs a switch-control signal to control each of the differential switches and each of the common-mode switches; when the switch-control signal is higher than a standard value, the plurality of differential switches are turned on and the plurality of common-mode switches are turned off; when the switch-control signal is lower than the standard value, the plurality of differential switches are turned off and the plurality of common-mode switches are turned on.

Preferably, the neural-signal amplifier further includes a bias-voltage generating unit electrically connected to the two switched-capacitor feedback-circuit units and the switched-capacitor circuit-output unit, and configured to generate the fifth bias and supply the fifth bias to the two switched-capacitor feedback-circuit units, and generate the fifth bias and the first bias and supply the fifth bias and the first bias to the switched-capacitor circuit-output unit. The bias-voltage generating unit is connected to a plurality of different bias sources.

Preferably, the bias-voltage generating unit includes a power-supply circuit formed by a Sooch Cascode current mirror.

Preferably, the amplifier includes an amplification circuit formed by a fully-differential folded common-source gate amplifier (FDFC Amp).

On the basis of the aforementioned purpose, the present invention further provides a multi-channel neural-signal amplifying system including a plurality of neural-signal amplifier coupling units, a plurality of analog-signal microprocessors, and a plurality of neural signal-sensing channels. Each of the neural-signal amplifier coupling units includes a plurality of neural-signal amplifiers. Each of the analog-signal microprocessors is coupled to one of the neural-signal amplifier coupling units, and each of the neural signal-sensing channels is connected to one of the neural-signal amplifiers.

One of the advantages of the aforementioned embodiment is that the switched capacitors are used to replace the external DC shielding capacitors, and the switched capacitors and switches may be configured to be constituted by transistors, thus minimizing the area of the overall integrated circuit. In addition, with the operation of the switched capacitors, the leakage current of the DC shielding capacitors may be reduced to further effectively reduce neural signal distortion.

Another advantage of the aforementioned embodiment is that a suppression circuits may be designed according to the DC drift range of the signal received in the signal terminal of the neural-signal amplifier of the circuit architecture with the switched-capacitor circuit-input unit.

Another advantage of the aforementioned embodiment is that, with the physiological signal-receiving channel architecture of the neural-signal amplifier independently disposed for each sensing channel, the neural signal received by the neural-signal amplifier with the multi-channel neural-signal acquisition architecture of the present invention may be more accurate, and the sensing signal of the analog front-end circuit may be more easily detected by the physiological signal-detecting terminal.

Another advantage of the aforementioned embodiment is that the detecting range of the stable measurement of the neural-signal amplifier circuit of the present invention may be adjusted by just adjusting the switched capacitors in the circuit architecture of the neural-signal amplifier of the present invention, so as to measure other physiological signal source. In addition, in the circuit architecture of the neural-signal amplifier of the present invention, the amplified gain range of the designed multi-channel neural-signal acquisition architecture may be adjusted by adjusting the circuit disposition of the switched capacitors in the output unit.

Another advantage of the aforementioned embodiment is that in the circuit architecture of the neural-signal amplifier of the present invention, mismatch between different current circuits in the neural-signal amplifier may be eliminated by using the bias-voltage generating unit to generate the plurality of biases for the switched-capacitor circuit-input unit and the switched capacitor feedback-circuit unit; furthermore, the power consumption of the overall circuit architecture may also be minimized.

Another advantage of the aforementioned embodiment is that in the circuit architecture of the neural-signal amplifier of the present invention, the accuracy of the signal gain may be further enhanced by sharing the differential amplifier of at least one bias source in the bias-voltage generating unit with the switched-capacitor circuit-input unit and the switched-capacitor feedback-circuit unit.

Other advantages of the present invention is to be explained in more detail together with descriptions and drawings as follows.

DESCRIPTION OF THE PREFERRED EMBODIMENTS

Figure 1:
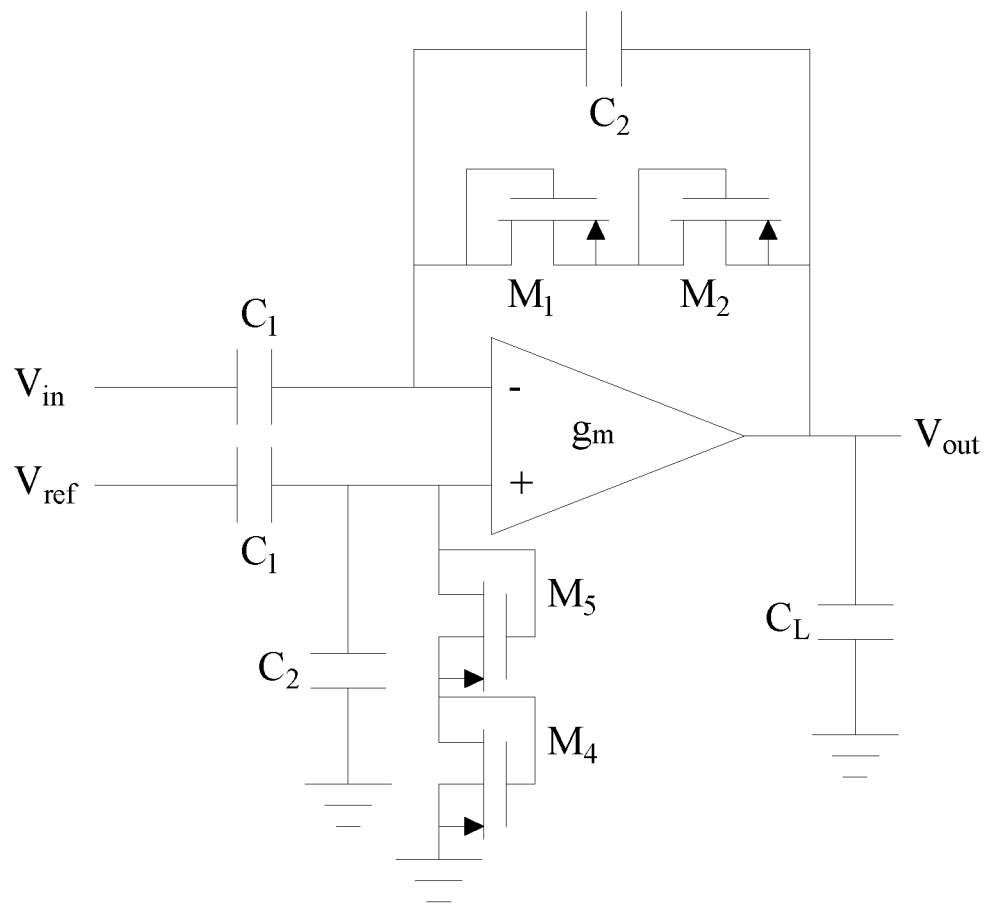
FIG. 1 depicts a circuit diagram of a conventional neural-signal detecting circuit.

The embodiment of the present invention is to be illustrated together with related drawings. In the drawings, the same symbols refer to the same or similar elements or method procedures.

Figure 2:
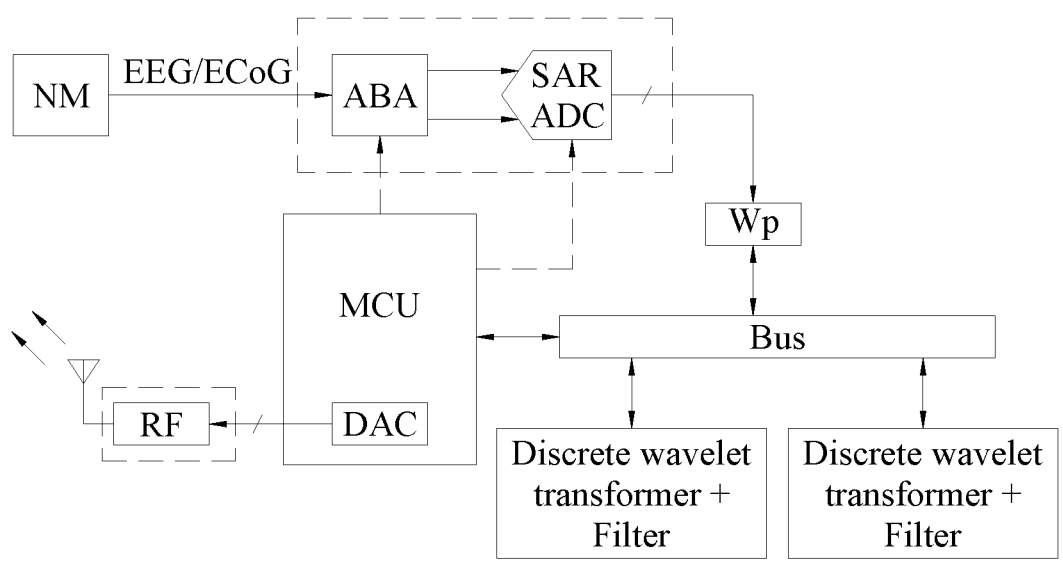
FIG. 2 depicts an architecture diagram of a brain neural electrophysiological signal-sensing system.

Please refer to FIG. 2, which depicts an architecture diagram of a brain neural electrophysiological signal-sensing system. As shown in FIG. 2, in the brain neural electrophysiological signal-sensing system, a neural-signal detector NM for sensing physiological signals, such as a neural-signal probe, may be used to transmit EEG/ECoG signals to an analog-biological signal-acquisition device ABA. An analog-digital converter ADC and a successive approximation register SAR may be used to convert analog signals into digital signals and then transmit the converted signals to a packet device WP and further to the bus BUS. A microcontroller MCU is connected to bus BUS, and includes a digital-to-analog signal converter DAC. The sensed physiological signals may be analyzed based on the converted amplified signals transmitted by an antenna RF.

Figure 3:
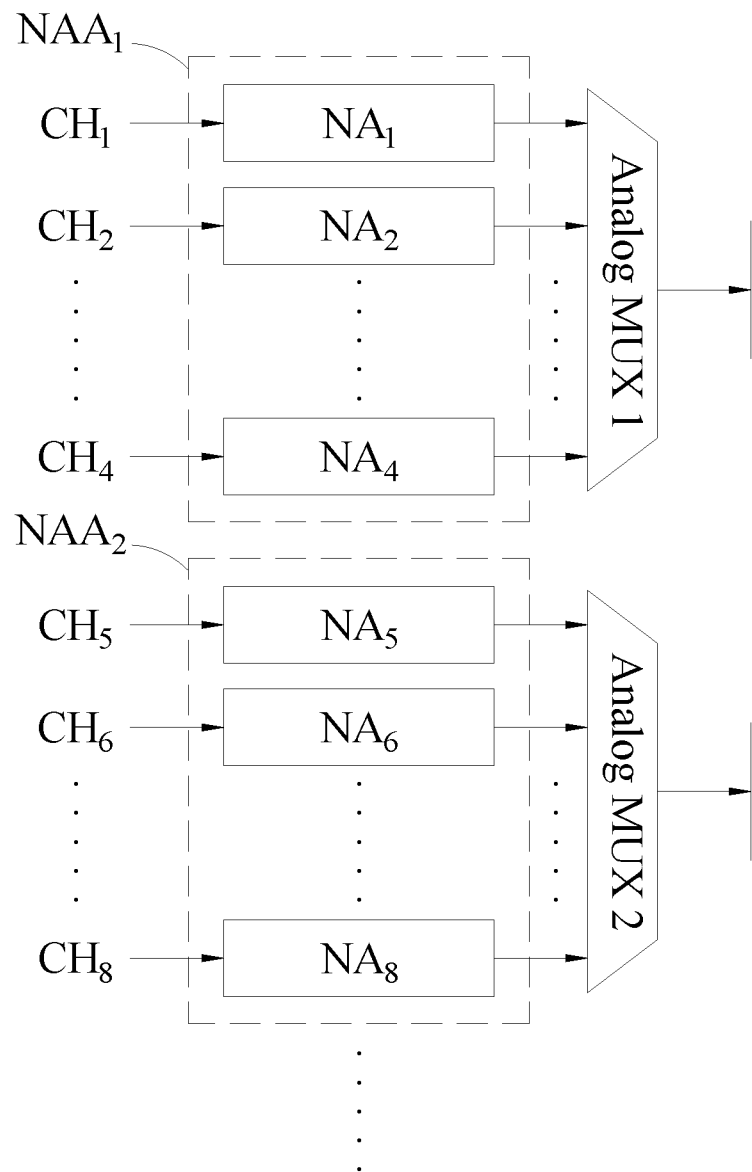
FIG. 3 depicts an architecture diagram of a multi-channel system according to an embodiment of the present invention.

Please refer to FIG. 3, which depicts an architecture diagram of the multi-channel system of the neural-signal amplifier according to an embodiment of the present invention. As shown in FIG. 3, a first neural-signal amplifier coupling unit $NAA_1$ includes a plurality of neural-signal amplifiers, such as the first neural-signal amplifier $NA_1$, the second neural-signal amplifier $NA_2$ to the fourth neural-signal amplifier $NA_4$. The first neural-signal amplifier $NA_1$ is connected to the first channel $Ch_1$, and the second neural-signal amplifier $NA_2$ is connected to the second channel $Ch_2$. In other words, in the first neural-signal amplifier coupling unit $NAA_1$, every neural-signal amplifier is independently connected to a channel, and each amplified signal in each neural-signal amplifier is further transmitted to a first analog-signal microprocessor Analog MUX1.

Furthermore, as shown in the embodiment of FIG. 3, the second neural-signal amplifier coupling unit $NAA_2$ includes a plurality of neural signal-sensing channels, and each neural signal-sensing channel is connected to one of the neural-signal amplifiers. The fifth neural-signal amplifier $NA_5$, and the sixth neural-signal amplifier $NA_6$ to the eighth neural-signal amplifier $NA_8$ are respectively and independently connected to the fifth channel $Ch_5$, and the sixth channel $Ch_6$ to the eighth channel $Ch_8$, and each amplified signal is further transmitted to a second analog-signal microprocessor Analog MUX2. However, the present invention is not limited to the examples described herein. Every neural-signal amplifier coupling unit may be further provided with more than four neural-signal amplifiers, and each neural-signal amplifier is independently connected to a physiological signal channel, and every neural-signal amplifier coupling unit is connected to an analog-signal microprocessor.

Figure 4:
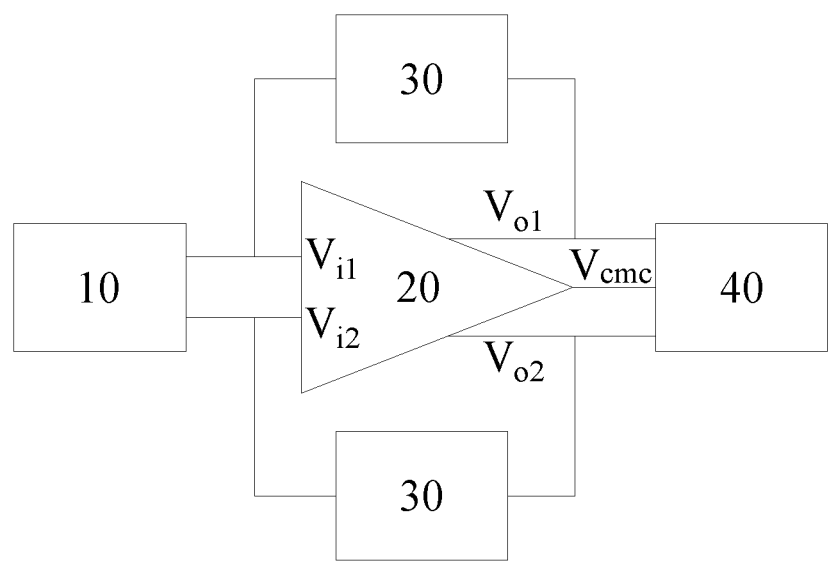
FIG. 4 depicts an block diagram of a neural-signal amplifier according to an embodiment of the present invention.

Please refer to FIG. 4, which depicts a block diagram of a neural-signal amplifier according to an embodiment of the present invention. As shown in FIG. 4, the neural-signal amplifier includes an amplifier 20, a switched-capacitor feedback-circuit unit 30, a switched-capacitor circuit-output unit 40, and a switched-capacitor circuit-input unit 10. The amplifier 20 includes a first input terminal $V_{i1}$, a second input terminal $V_{i2}$, a first output terminal $V_{o1}$, a second output terminal $V_{o2}$, and a common-mode feedback-input terminal $V_{cmc}$.

The switched-capacitor circuit-input unit 10 is connected to the first input terminal $V_{i1}$ and the second input terminal $V_{i2}$ of the amplifier 20. The switched-capacitor circuit-output unit 40 is connected to the common-mode feedback-input terminal $V_{cmc}$, the first output terminal $V_{o1}$, and the second output terminal $V_{o2}$ of the amplifier 20. One switched-capacitor feedback-circuit unit 30 has a terminal connected between the first output terminal $V_{o1}$ and the switched-capacitor circuit-output unit 40, and the other terminal connected between the first input terminal $V_{i1}$ and the switched-capacitor circuit-input unit 10. The other switched-capacitor feedback-circuit unit 30 has a terminal connected to the second output terminal $V_{o2}$ and the switched-capacitor circuit-output unit 40, and the other terminal connected between the second input terminal $V_{i2}$ and the switched-capacitor circuit-input unit 10.

In some embodiments of the present invention, the amplifier includes an amplification circuit formed by a fully-differential folded common-source gate amplifier (FDFC Amp).

As shown in FIG. 4, the amplifier 20 includes a first input terminal $V_{i1}$, a second input terminal $V_{i2}$, a first output terminal $V_{o1}$, a second output terminal $V_{o2}$, and a common-mode feedback-input terminal $V_{cmc}$. The first input terminal $V_{i1}$ receives the first input signal, the second input terminal $V_{i2}$ receives the second input signal, and the common-mode feedback-input terminal $V_{cmc}$ receives the common-mode feedback-input signal. The first amplified output signal and the second amplified output signal are respectively outputted from the first output terminal $V_{o1}$ and the second output terminal $V_{o2}$.

The switched-capacitor circuit-input unit 10 receives a first bio-potential signal and a second bio-potential signal to generate the first input signal and the second input signal. The two switched-capacitor feedback-circuit units 30 are electrically connected between the first input terminal $V_{i1}$ and the first output terminal $V_{o1}$, and between the second input terminal $V_{i2}$ and the second output terminal $V_{o2}$ of the amplifier 20. The switched-capacitor circuit-output unit 40 receives the first amplified output signal and the second amplified output signal to generate the common-mode feedback-input signal.

Figure 5:
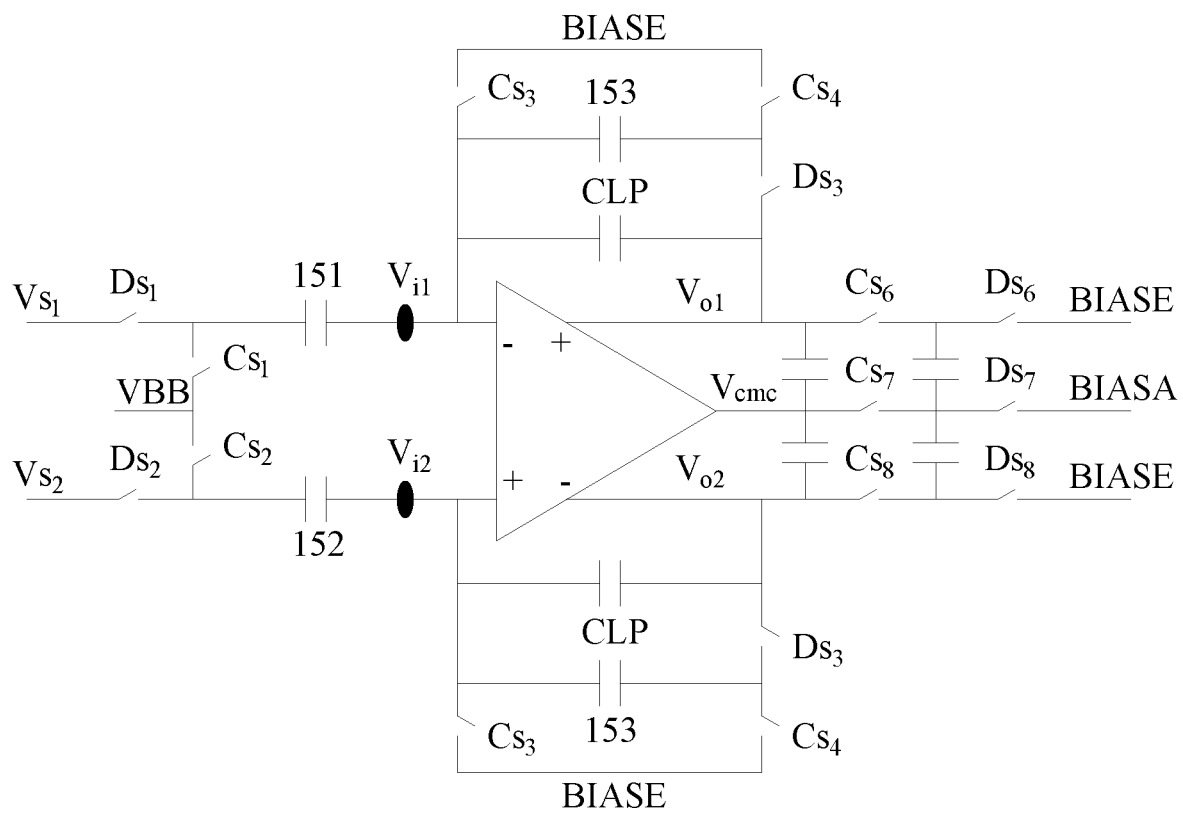
FIG. 5 depicts a circuit diagram of a neural-signal amplifier according to an embodiment of the present invention.

Please further refer to FIG. 5, which depicts a circuit diagram of the neural-signal amplifier according to an embodiment of the present invention. The configuration of the switched-capacitor circuit-input unit 10 according to an embodiment of the present invention is to be described as follows. As shown in FIG. 5, the switched-capacitor circuit-input unit 10 includes a first differential switch $Ds_1$, a first common-mode switch $Cs_2$, a second differential switch $Ds_2$, a second common-mode switch $Cs_2$, a first capacitor 151, and a second capacitor 152, and the switched-capacitor circuit-input unit 10 is connected to a first reference voltage source that supplies a first reference voltage BIASA. The first differential switch $Ds_1$ is connected to the first bio-potential signal terminal $V_{S1}$ that receives a first bio-potential signal. The first common-mode switch $Cs_1$ is connected between the first differential switch $Ds_1$ and the first capacitor 151. The first capacitor 151 is connected to the first input terminal $V_{i1}$. The second differential switch $Ds_2$ is connected to a second bio-potential signal terminal $V_{S2}$ that receives a second bio-potential signal. The second common-mode switch $Cs_2$ is connected between the second differential switch $Ds_2$ and the second capacitor 152. The second capacitor 152 is connected to the second input terminal $V_{i2}$. The first reference voltage BIASA is supplied between the first common-mode switch $Cs_1$ and the second common-mode switch $Cs_2$.

In some embodiments of the present invention, the first differential switch $Ds_1$, the first common-mode switch $Cs_2$, the second differential switch $Ds_2$, the second common-mode switch $Cs_2$, the first capacitor 151, and the second capacitor 152 can be formed by transistors. This further minimizes the size of the neural-signal amplifier of the present invention in the chip architecture.

The configuration of the switched-capacitor feedback-circuit unit 30 according to an embodiment of the present invention is to be described as follows. The switched-capacitor feedback-circuit unit 30 includes a third common-mode switch $Cs_3$, a fourth common-mode switch $Cs_4$, a third differential switch $Ds_3$, a third capacitor 153, a low-pass capacitor CLP, and the switched-capacitor feedback-circuit unit 30 is connected to a fifth bias source which supplies a fifth bias BIASE. The fourth common-mode switch $Cs_4$ is connected to the fifth bias source that supplies the fifth bias BIASE, the fifth bias source is also connected to the third common-mode switch $Cs_3$, and the third differential switch $Ds_3$ is connected to the fourth common-mode switch $Cs_4$. The third capacitor 153 is connected between the third common-mode switch $Cs_3$ and the fourth common-mode switch $Cs_4$. The low-pass capacitor CLP is connected between the third common-mode switch $Cs_3$ and the third differential switch $Ds_3$.

Specifically, in an embodiment of the present invention, the neural-signal amplifier 1 includes two switched-capacitor feedback-circuit units; the third capacitor 153, the low-pass capacitor CLP, and the third common-mode switch $Cs_3$ of one switched-capacitor feedback-circuit unit 30 are connected to the first input terminal $V_{i1}$, and the low-pass capacitor CLP and the fourth common-mode switch $Cs_4$ of this one switched-capacitor feedback-circuit unit 30 are connected to the first output terminal $V_{o1}$.

The third capacitor 153, the low-pass capacitor CLP, and the third common-mode switch $Cs_3$ of the other switched-capacitor feedback-circuit unit 30 are connected to the second input terminal $V_{i2}$. The low-pass capacitor CLP and the fourth common-mode switch $Cs_4$ of the other switched-capacitor feedback-circuit unit 30 are connected to the second output terminal $V_{o2}$.

Thus, the feedback circuits having the first input terminal $V_{i1}$, the first output terminal $V_{o1}$, the second input terminal $V_{i2}$, and the second output terminal $V_{o2}$ are respectively configured to suppress DC current drift.

In some embodiments of the present invention, the low-pass capacitor CLP, the third common-mode switch $Cs_3$, and the fourth common-mode switch $Cs_4$ are configured to be formed by transistors, so as to minimize the size of the neural-signal amplifier of the present invention in the chip architecture.

The configuration of the switched-capacitor circuit-output unit 40 is to be further described below. The switched-capacitor circuit-output unit 40 includes a plurality of capacitors and switches and is connected to at least one voltage source. In an embodiment of the present invention, the switched-capacitor circuit-output unit 40 includes a sixth common-mode switch $Cs_6$, a seventh common-mode switch $Cs_7$, an eighth common-mode switch $Cs_8$, a sixth differential switch $Ds_6$, a seventh differential switch $Ds_7$, an eighth differential switch $Ds_8$, a fifth capacitor 155, a sixth capacitor 156, a seventh capacitor 157, and an eighth capacitor 158. In addition, the switched-capacitor circuit-output unit 40 is also connected to the fifth bias source that supplies the fifth bias BIASE, and the first bias source that supplies the first bias BIASA.

Further, the sixth common-mode switch $Cs_6$ is connected to the first output terminal $V_{o1}$; the seventh common-mode switch $Cs_7$ is connected to the common-mode feedback-input terminal $V_{cmc}$; the eighth common-mode switch $Cs_8$ is connected to the second output terminal $V_{o2}$; one terminal of the sixth differential switch $Ds_6$ is connected to the sixth common-mode switch $Cs_6$, and the other terminal thereof is connected to the fifth bias source which supplies the fifth bias BIASE; one terminal of the seventh differential switch $Ds_7$ is connected to the seventh common-mode switch $Cs_7$, and the other terminal thereof is connected to the first bias source which supplies the first bias BIASA; one terminal of the eighth differential switch $Ds_8$ is connected to the eighth common-mode switch $Cs_8$, and the other terminal thereof is connected to the fifth bias source which supplies the fifth bias BIASE.

Figure 6:
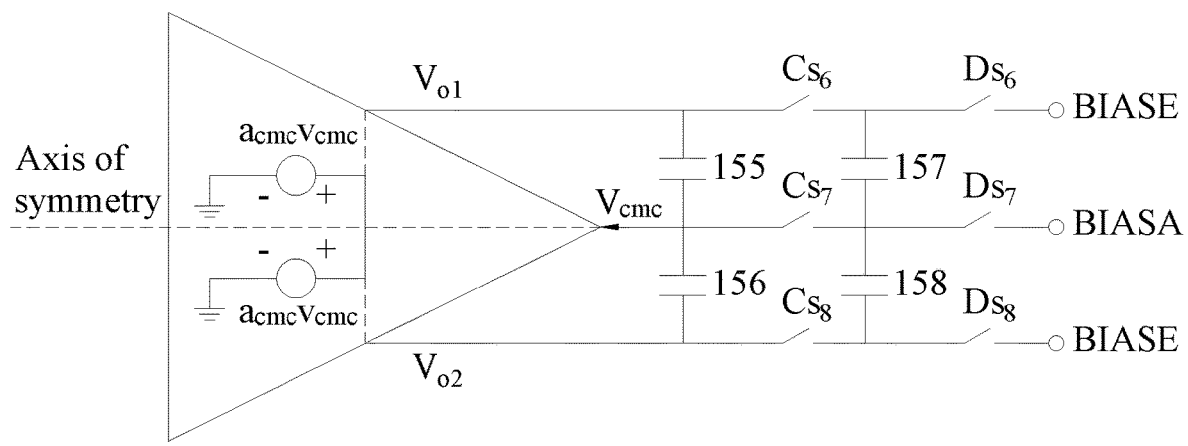
FIG. 6 depicts a circuit diagram of a common-mode feedback-input architecture according to an embodiment of the present invention.

Please refer to FIG. 6, the connection configuration of the plurality of capacitors in the switched-capacitor circuit-output unit 40 is that one terminal of the fifth capacitor 155 is connected between the first output terminal $V_{o1}$ and the seventh common-mode switch $Cs_7$, and the other terminal of the fifth capacitor 155 is connected between the common-mode feedback-input terminal $V_{cmc}$ and the seventh differential switch Ds$_7$; one terminal of the sixth capacitor 156 is connected between the common-mode feedback-input terminal V$_{cmc}$ and the seventh common-mode switch Cs$_7$, and the other terminal of the sixth capacitor 156 is connected between the second output terminal V$_{o2}$ and the eighth common-mode switch Cs$_8$; the seventh capacitor 157 is connected between the sixth common-mode switch Cs$_6$ and the eighth differential switch Ds$_8$, and the other terminal of the seventh capacitor 157 is connected between the seventh common-mode switch Cs$_7$ and the seventh differential switch Ds$_7$; one terminal of the eighth capacitor 158 is connected between the seventh common-mode switch Cs$_7$ and the seventh differential switch Ds$_7$, and the other terminal of the eighth capacitor 158 is connected between the eighth common-mode switch Cs$_8$ and the eighth differential switch Ds$_8$. When the differential switches Ds$_1$ to Ds$_8$ are turned on and the common-mode switches Cs$_1$ to Cs$_8$ are turned off, the neural-signal amplifier of the present invention is in a differential amplifying state; when the differential switches Ds$_1$ to Ds$_8$ are turned off and the common-mode switches Cs$_1$ to Cs$_8$ are turned on, the neural-signal amplifier of the present invention is in a common-mode reconstructing state.

The method of generating the common-mode feedback-input signal outputted by the switched-capacitor circuit-output unit 40 is to be further described as follows. Please refer to FIG. 6 and FIG. 7 which depict a circuit diagram of the common-mode feedback-input architecture, and a half-circuit diagram of the common-mode feedback-input architecture in FIG. 6 according to an embodiment of the present invention, respectively. In the common-mode feedback-input architecture illustrated in FIG. 6, the elements are symmetrically disposed along the direction of the common-mode feedback input, thus preventing the common-mode feedback input from being interfered by differential signals. In other words, in the circuit architecture illustrated in FIG. 6, the circuit architecture may be a fine common-mode feedback circuit by making the direction of the common-mode feedback input (V$_{cmc}$) the same as the direction to which the symmetrical axis of the whole circuit extends.

Furthermore, the output voltage of the common-mode feedback circuit is designed to be (V$_{oc}$-V$_{cm}$). In an embodiment of the present invention, the common-mode feedback-input circuit is designed by the configuration of the switchable switches and capacitors to construct the common-mode feedback input, which has smaller limitation on amplifier output signal amplitudes compared to a conventional 2-differential-pairs common-mode feedback circuit and a triode-region transistor common-mode feedback circuit. In addition, the switched-capacitor common-mode feedback circuit of the present invention does not need to withstand higher resistance loading unlike a conventional resistive-divider common-mode feedback circuit does.

Furthermore, the switched-capacitor common-mode feedback circuit of the present invention may be further applied to a capacitor-filter circuit or other amplifier circuits.

FIG. 6 shows a common-mode feedback circuit diagram. The plurality of switches can be controlled to change the path of the switches for receiving the fifth bias. Preferably, the first bias BIASA is a DC bias; the fifth capacitor 155, the sixth capacitor 156, the seventh capacitor 157, and the eighth capacitor 158 receive the fifth bias BIASE with the deduction of the first bias BIASA.

The first bias BIASA is the DC bias voltage. The sixth common-mode switch Cs$_6$, the seventh common-mode switch Cs$_7$, the eighth common-mode switch Cs$_8$, the sixth differential switch Ds$_6$, the seventh differential switch Ds$_7$, and the eighth differential switch Ds$_8$ can be formed by transistors, and controlled by two non-overlapping clock signals, so as to minimize the size of the neural-signal amplifier of the present invention in the chip architecture.

Figure 7:
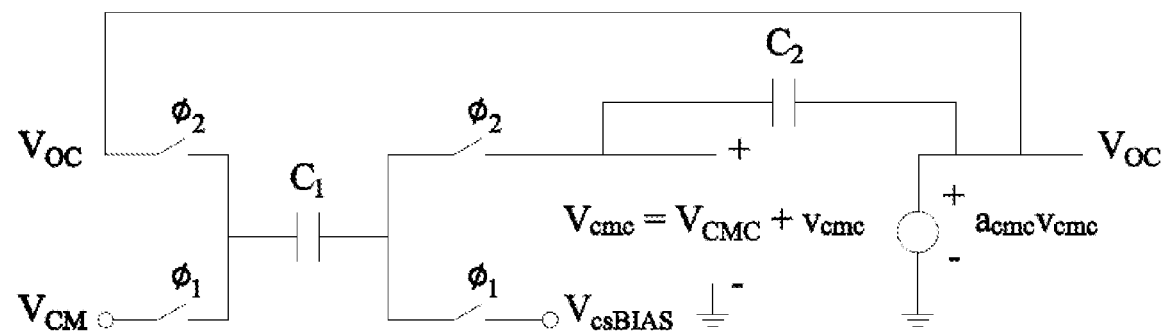
FIG. 7 depicts a half-circuit diagram of the common-mode feedback-input architecture according to an embodiment of the present invention.

FIG. 7 discloses a simplified OP amplifier model of the common-mode feedback-input architecture of FIG. 6. The common-mode feedback-input circuit constituted by the switched capacitors is a linear and balanced discrete-time circuit. The second capacitor C2 is connected between the common-mode feedback voltage terminal V$_{cmc}$ and the output voltage V$_{oc}$, and the voltage gain is denoted as A$_{cmc}$. When the switches are switched such that all switches corresponding to the first phase f1 are turned on and those corresponding to the second phase f2 are turned off, the supplied voltage received by the first capacitor C1 is V$_{CM}$-V$_{CSBIAS}$. When the switches are switched such that all switches corresponding to the first phase f1 are turned off and those corresponding to the second phase f2 are turned on, the first capacitor C1 is connected between the output voltage V$_{oc}$ and the common-mode bias voltage V$_{cmc}$. In a stable state, V$_{oc}$ is a constant value because the common-mode bias voltage V$_{CM}$ and the reference voltage V$_{CSBIAS}$ applied during the operation are both DC voltages, and the switched-capacitor circuit operates under a negative feedback loop.

When the output voltage V$_{oc}$ is constant, the charge transfer halt in the clock phase may be presented as follows:

$$Q(\Phi_1)=C_1(V_{CM}-V_{CSBIAS})=Q(\Phi_2)=C_1(V_{oc}-V_{cmc})$$
$$\Rightarrow V_{CM}-V_{CSBIAS}=V_{oc}-V_{cmc}$$

When the base-bias voltage V$_{CSBIAS}$ is equal to the common-mode bias voltage V$_{CM}$ and the voltage gain A$_{cmc}$ is much greater than 1, the common-mode bias voltage V$_{CM}$ approaches the base-bias voltage V$_{CSBIAS}$ and the output voltage V$_{oc}$ approaches the common-mode bias voltage V$_{CM}$. In other words, since the switched-capacitor circuit is only formed by passive elements such as capacitors and switches, the common-mode circuit is not limited by the output voltage amplitude of the op amplifier.

Figure 8:
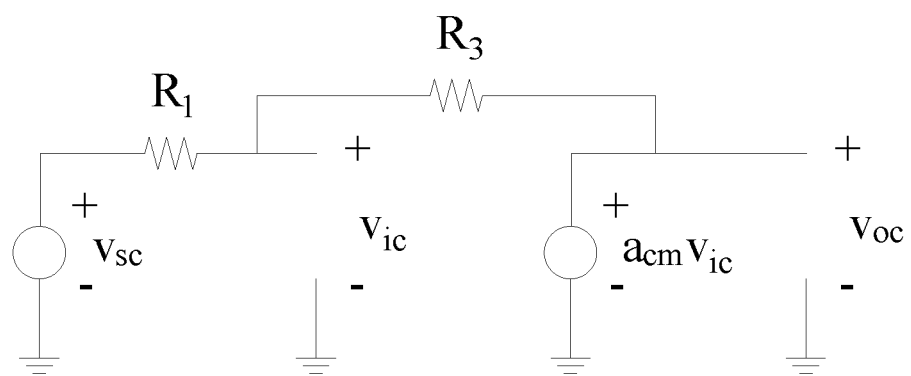
FIG. 8 depicts a half-circuit architecture diagram of a reconstructed common-mode DC power input according to an embodiment of the present invention.

Please refer to FIG. 8, which depicts a half-circuit architecture diagram of the reconstructed common-mode DC power input according to an embodiment of the present invention. As shown, in the ideal fully-differential operational model, the gain of the common-mode half circuit is A$_{cmc}$=0, and thus the overall closed-loop common-mode gain is zero. Therefore, the output voltage V$_{oc}$ of the common-mode circuit is independent from the input voltage V$_{ic}$ and the common-mode source voltage V$_{sc}$ of the common-mode operational amplifier. In actual application, the gain A$_{cmc}$ of the OP amplifier in the common-mode half-circuit is not zero but is small enough. By using the input differential pair and the tail current source, a common-mode feedback amplification loop may be added to the circuit, so as to reconstruct the input common-mode voltage, thus preventing the input common-mode voltage from possibly drifting.

Figure 9:
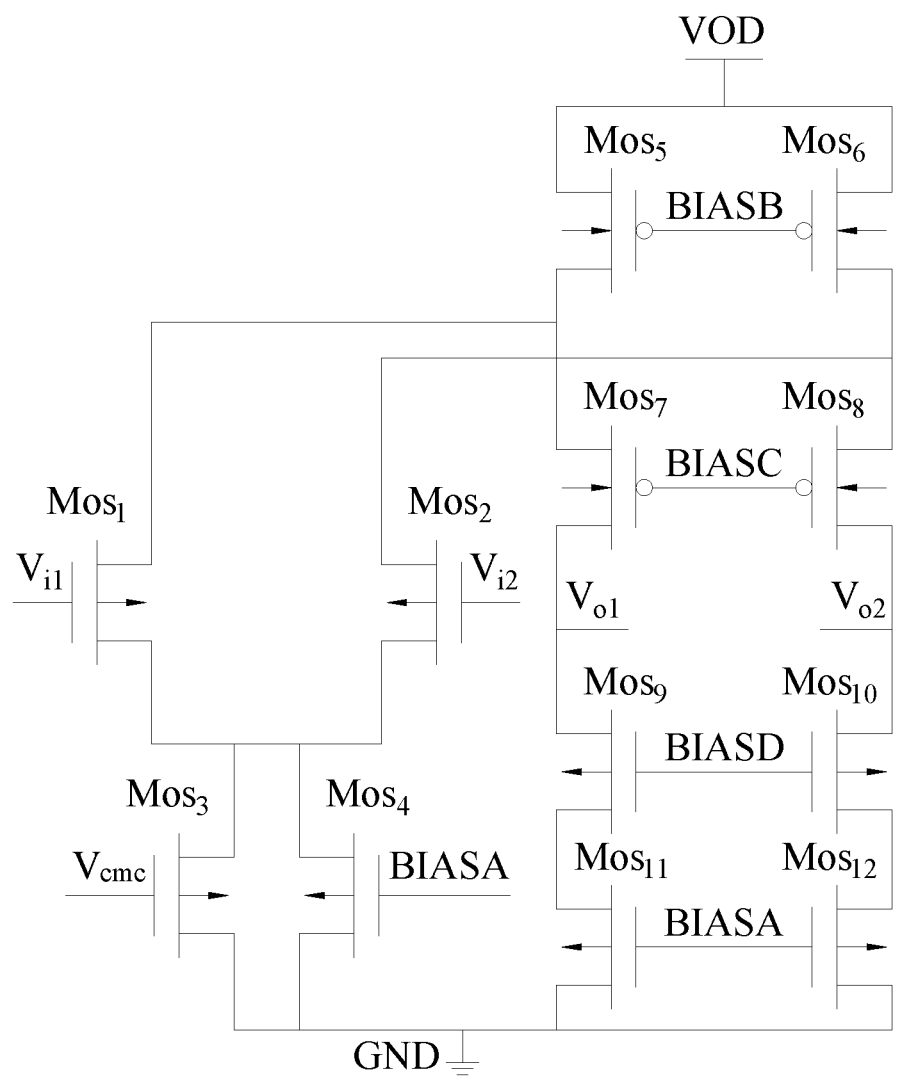
FIG. 9 depicts a circuit diagram of a switched-capacitor circuit-output unit according to an embodiment of the present invention.

Please refer to FIG. 9, which depicts a circuit diagram of the switched-capacitor circuit-output unit according to an embodiment of the present invention. As shown in FIG. 9, this switched-capacitor circuit-output unit includes a first transistor Mos$_1$, a second transistor Mos$_2$, a third transistor Mos$_3$, a fourth transistor Mos$_4$, a fifth transistor Mos$_5$, a sixth transistor Mos$_6$, a seventh transistor Mos$_7$, an eighth transistor Mos$_8$, a ninth transistor Mos$_9$, a tenth transistor Mos$_{10}$, an eleventh transistor Mos$_{11}$, and a twelfth transistor Mos$_{12}$.

Specifically, in an embodiment of the present invention, the gate of the first transistor Mos$_1$ is connected to the first input voltage $V_{i1}$; the gate of the second transistor $Mos_2$ is connected to the second input voltage $V_{i2}$; the gate of the third transistor $Mos_3$ is connected to the common-mode feedback-input terminal $V_{cmc}$; the gate of the fourth transistor $Mos_4$ is connected to the first bias BIASA; the gates of the fifth transistor $Mos_5$ and the sixth transistor $Mos_6$ are connected to the second bias BIASB; the gates of the seventh transistor $Mos_7$ and the eighth transistor $Mos_8$ are connected to the third bias BIASC; the gates of the ninth transistor $Mos_9$ and the tenth transistor $Mos_{10}$ are connected to the fourth bias BIASD; the gates of the eleventh transistor $Mos_{11}$ and the twelfth transistor $Mos_{12}$ are connected to the fifth bias BIASE.

Furthermore, as shown in FIG. 9, the fully-differential folded-cascode amplifier with a Sooch Cascode current mirror is used in a biasing operation. The switched-capacitor common-mode feedback circuit is configured to have a common-mode voltage. The gain $A_{dm0}$ of the low-frequency differential mode of the fully-differential folded-cascode amplifier may be denoted as follows:

$A_{dm0} = -gm1 \times R_{odh}$, wherein gm1 refers to the transconductance of the input transistors, and $R_{odh}$ refers to the output resistance of low-frequency differential half-circuit.

Furthermore, in the circuit architecture illustrated in FIG. 9, the output resistance $R_{odh}$ of the low-frequency differential half-circuit may also be denoted as $R_{odh} \approx [r_{o7}g_{m7}(r_{o5}//r_{o1})]//(r_{o9}g_{m9}r_{o11})$, wherein $r_o$ refers to the output resistance of the transistor, and the numbers refer to the corresponding transistors, for instance, $r_{o7}$ is the output resistance of the seventh transistor, $r_{o5}$ is the output resistance of the fifth transistor, $r_{o1}$ is the output resistance of the first transistor, $r_{o9}$ is the output resistance of the ninth transistor, and $r_{o11}$ is the output resistance of the eleventh transistor. gm refers to the transconductance of the transistor, and the numbers refer to the corresponding transistors, for instance, $gm_7$ is the transconductance of the seventh transistor, and $gm_9$ is the transconductance of the ninth transistor.

The gain of the low-frequency differential mode of the fully-differential folded-cascode amplifier may be denoted as follows:

$A_{cm0} = -g_{m1}/(1+g_{m1}R_t) \times R_{och} \approx -R_{och}/R_t$, wherein $gm_1$ is the transconductance of the input transistor, $R_{och}$ is the output resistance of the low-frequency common-mode half-circuit, and $R_t$ is the degenerated resistance of the input transistor.

Specifically, in the circuit architecture illustrated in FIG. 9, the output resistance of the low-frequency common-mode half-circuit is $R_{och} \approx [r_{o7}g_{m7}(r_{o5}//R_o(M1))]//(r_{o9}g_{m9}r_{o11})$, wherein $R_o(M1) \approx r_{o1}g_{m1}(2r_{o4}//2r_{o3})$. The degenerated resistance of the transistor as stated above is $R_t \approx (2r_{o4}//2r_{o3})$.

In an embodiment of the present invention, this circuit further includes a bias-voltage generating unit. The bias-voltage generating unit is electrically connected to the two switched-capacitor feedback-circuit units 30 and the switched-capacitor circuit-output unit 40, generates the fifth bias BIASE and supplies the fifth bias BIASE to the two switched-capacitor feedback-circuit units, and generates the fifth bias BIASE and the first bias BIASA and supplies the fifth bias BIASE and the first bias BIASA to the switched-capacitor circuit-output unit 40. The bias-voltage generating unit is connected to a plurality of different bias sources.

In some embodiments of the present invention, the bias-voltage generating unit includes a power-supply circuit constituted by a Sooch Cascode current mirror.

Figure 10:
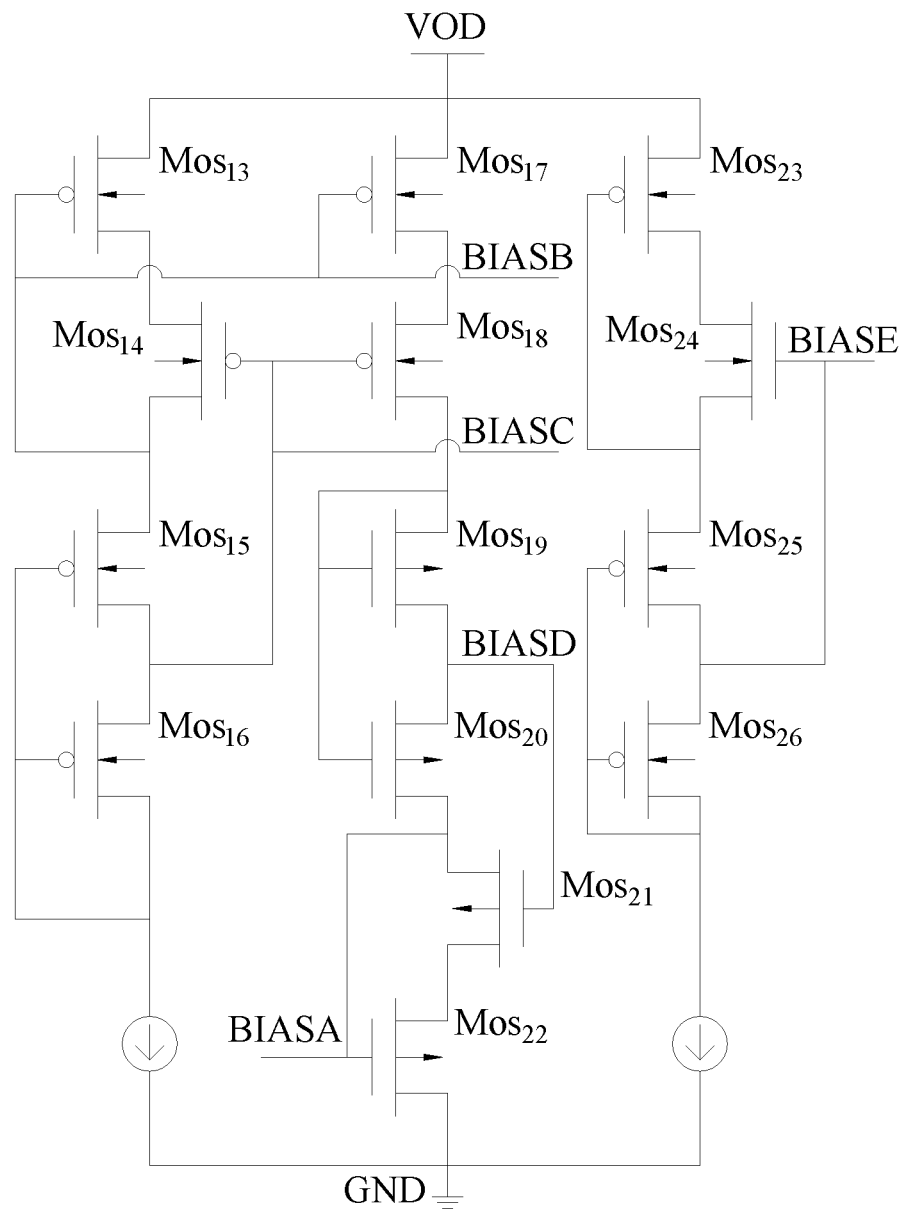
FIG. 10 depicts a circuit diagram of a bias-voltage generating unit according to an embodiment of the present invention.

Please refer to FIG. 10, which depicts a circuit diagram of the bias-voltage generating unit according to an embodiment of the present invention. As shown in FIG. 10, this bias-voltage generating unit includes a thirteenth transistor $Mos_{13}$, a fourteenth transistor $Mos_{14}$, a fifteenth transistor $Mos_{15}$, a sixteenth transistor $Mos_{16}$, a seventeenth transistor $Mos_{17}$, an eighteenth transistor $Mos_{18}$, a nineteenth transistor $Mos_{19}$, a twentieth transistor $Mos_{20}$, a twenty-first transistor $Mos_{21}$, a twenty-second transistor $Mos_{22}$, a twenty-third transistor $Mos_{23}$, a twenty-fourth transistor $Mos_{24}$, a twenty-fifth transistor $Mos_{25}$, and a twenty-sixth transistor $Mos_{26}$.

Specifically, as shown in FIG. 10, the gate of the thirteenth transistor $Mos_{13}$ and the gate of the seventeenth transistor $Mos_{17}$ are connected to the second bias BIASB; the gate of the fourteenth transistor $Mos_{14}$ and the gate of the eighteenth transistor $Mos_{18}$ are connected to the third bias BIASC; the gate of the fifteenth transistor $Mos_{15}$ is connected to the gate of the sixteenth transistor $Mos_{16}$; the gate of the nineteenth transistor $Mos_{19}$ is connected to the gate of the twentieth transistor $Mos_{20}$; the gate of the twenty-first transistor $Mos_{21}$ is connected to the fourth bias BIASD; the gate of the twenty-second transistor $Mos_{22}$ is connected to the first bias BIASA; the gate of the twenty-third transistor $Mos_{23}$ is connected between the twenty-fourth transistor $Mos_{24}$ and the twenty-fifth transistor $Mos_{25}$; the gate of the twenty-fourth transistor $Mos_{24}$ is connected to the fifth bias BIASE; the gate of the twenty-fifth transistor $Mos_{25}$ is connected to the gate electrode of the twenty-sixth transistor $Mos_{26}$.

Furthermore, as shown in the circuit architecture disclosed in FIG. 10, this circuit not only provides extremely high output resistance, but also combines the input current branch, thus eliminating mismatch between each current branch and reducing the consumed power.

Figure 11:
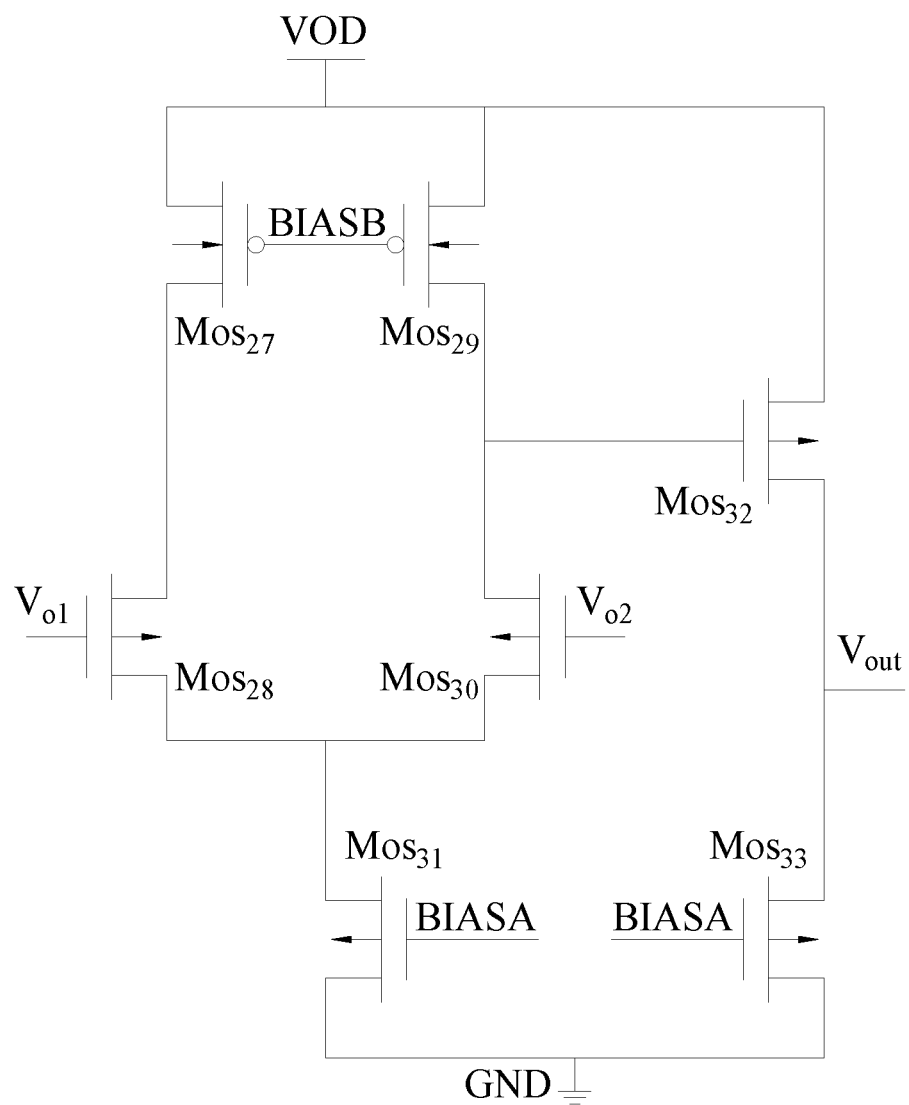
FIG. 11 depicts a circuit diagram of a two-stage amplification unit according to an embodiment of the present invention.

Please refer to FIG. 11, which depicts a circuit diagram of the two-stage amplification unit according to an embodiment of the present invention. As shown in FIG. 11, this two-stage amplification unit includes a twenty-seventh transistor $Mos_{27}$, a twenty-eighth transistor $Mos_{28}$, a twenty-ninth transistor $Mos_{29}$, a thirtieth transistor $Mos_{30}$, a thirty-first transistor $Mos_{31}$, a thirty-second transistor $Mos_{32}$, and a thirty-third transistor $MOS_{33}$.

The gate of the twenty-seventh transistor $Mos_{27}$ and the gate of the twenty-ninth transistor $Mos_{29}$ are connected to the second bias BIASB; the gate of the twenty-eighth transistor $Mos_{28}$ is connected to the first output terminal $V_{o1}$; the gate of the thirtieth transistor $Mos_{30}$ is connected to the second output terminal $V_{o2}$; the gate of the thirty-first transistor $Mos_{31}$ is connected to the first bias BIASA; the gate of the thirty-third transistor $Mos_{33}$ is connected to the first bias BIASA; the gate of the thirty-second transistor $Mos_{32}$ is connected between the twenty-ninth transistor $Mos_{29}$ and the thirtieth transistor $Mos_{30}$.

Specifically, with configuration of the two-stage amplification unit circuit as shown in FIG. 11, the input signal is differentially amplified by single-end amplification and two-stage amplification, so as to enhance the gain and benefit the external signal analysis.

Figure 12:
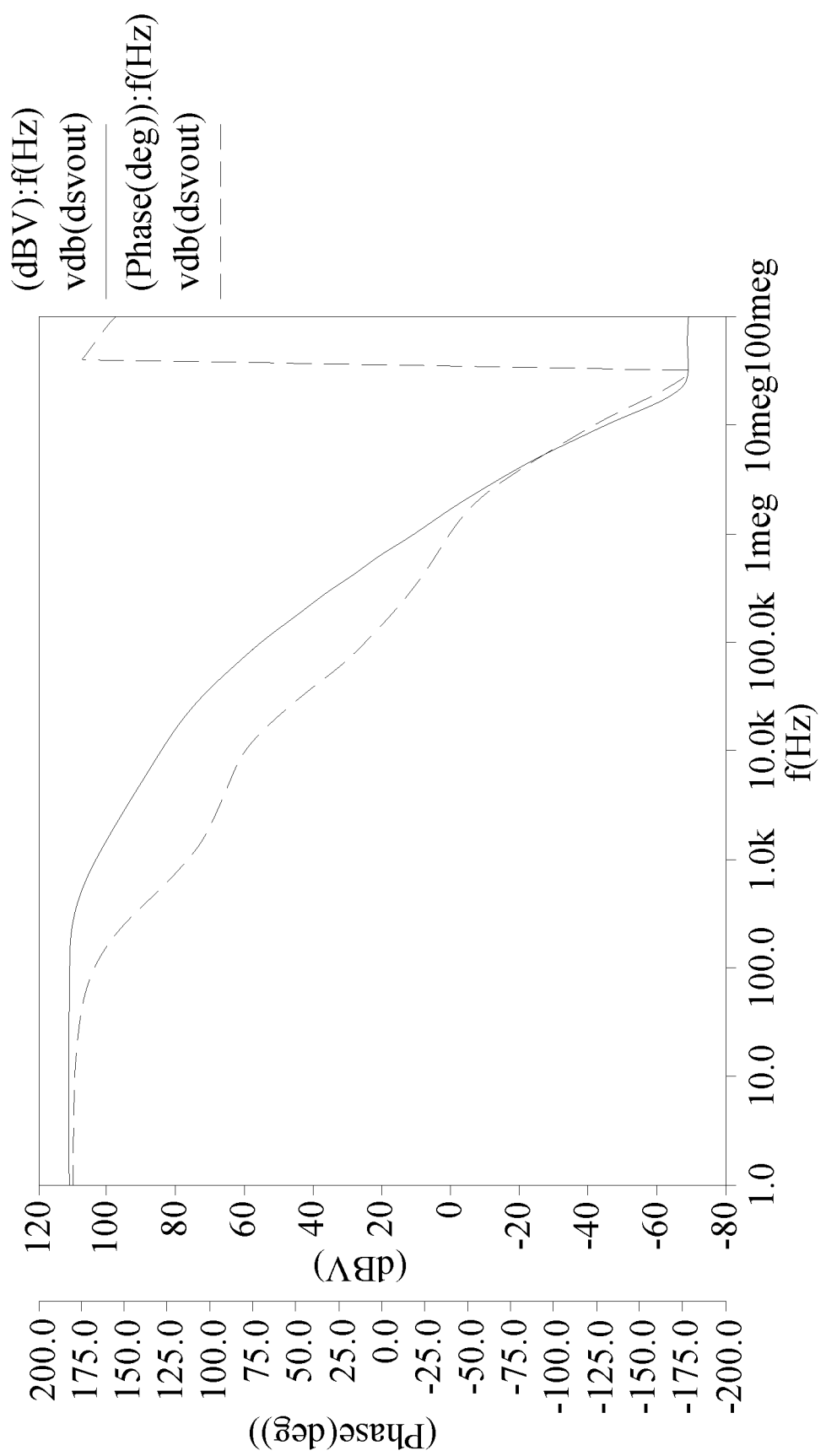
FIG. 12 depicts an open-loop frequency response diagram according to an embodiment of the present invention.

Please refer to FIG. 12, which depicts an open-loop frequency response diagram according to an embodiment of the present invention. As shown in FIG. 12, in an embodiment of the present invention, the open-loop frequency response of the neural-signal amplifier has a phase margin of 130 degrees at a bandwidth of BW=1.689 MHz. Furthermore, as shown in FIG. 12, the amplifying system may be stable at a phase margin of 60 degrees; the amplifying system may have a risk of oscillation at a phase margin lower than 60 degrees.

Figure 13:
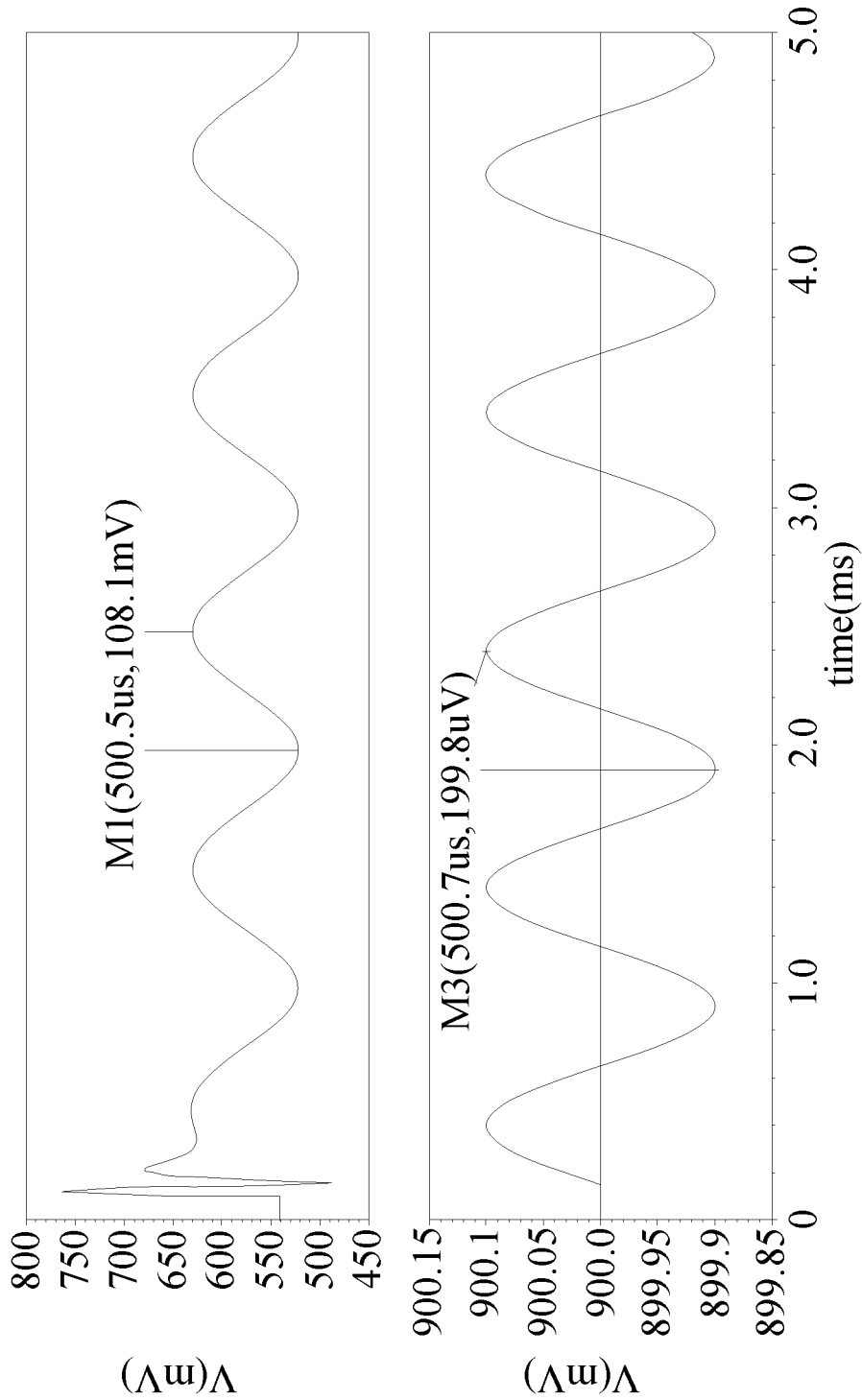
FIG. 13 depicts a time-domain transient response diagram according to an embodiment of the present invention.

Please refer to FIG. 13, which depicts a time-domain transient response diagram according to an embodiment of the present invention. As shown in FIG. 13, this diagram shows a time-domain transient response of the output signal of the single neural-signal amplifier when the input signal is [0.9+100 □V □ sin (1 KHz)].

In summary, in the present invention, the switched capacitors are used to replace the external DC shielding capacitors; in some embodiments, the switched capacitors and switches may be implemented by transistors, thus minimizing the area of the overall integrated circuit. In addition, with the operations of the switched capacitors, the leakage currents of the switched capacitors are lower than that of the DC shielding capacitors, so that neural signal distortion of the neural-signal amplifier of the present invention can be reduced.

Furthermore, the neural signal received by the multi-channel neural-signal acquisition architecture designed according to the neural-signal amplifier of the present invention may be more accurate, and the sensing signal of the analog front-end circuit may be more easily detected by the physiological signal-detecting terminal by the physiological signal-receiving channel architecture of the neural-signal amplifier independently disposed for each sensing channel.

In addition, the detecting range of the stable measurement of the neural-signal amplifier circuit and the gain range of the designed multi-channel neural-signal acquisition architecture of the present invention may be adjusted by adjusting the circuit disposition of the switched capacitors, so that the neural-signal amplifier of the present invention may be applied to measure other physiological signal sources.

The multi-channel neural-signal amplifying system of the present invention may further eliminate mismatch between different current circuits in the neural-signal amplifier by respectively using the bias-voltage generating unit, which generates the plurality of biases for the switched-capacitor circuit-input unit, and the switched capacitor feedback-circuit unit. Moreover, the accuracy of the signal amplification gain may be further enhanced and the power consumption of the overall circuit architecture can be reduced by sharing a plurality of voltage sources.

The present invention may be realized in different forms and should not be construed as limited to the embodiments set forth herein. On the contrary, the provided embodiments may make the present invention more easily understood and convey the scope of the present invention more thoroughly and completely for a person of ordinary skills in the art; the present invention may be defined by the scope of the appended claims.

What is claimed is:

1. A neural-signal amplifier, comprising:
an amplifier comprising a first input terminal, a second input terminal, a first output terminal, a second output terminal, and a common-mode feedback-input terminal, wherein the first input terminal is configured to receive a first input signal, the second input terminal is configured to receive a second input signal, and the common-mode feedback-input terminal is configured to receive a common-mode feedback-input signal to generate and respectively output a first amplified output signal and a second amplified output signal from the first output terminal and the second output terminal; and
a switched-capacitor circuit-input unit receiving a first bio-potential signal and a second bio-potential signal to generate the first input signal and the second input signal; and
two switched-capacitor feedback-circuit units, wherein one of the two switched-capacitor feedback-circuit units is electrically connected between the first input terminal and the first output terminal of the amplifier, and other one of the two switched-capacitor feedback-circuit units is electrically connected between the second input terminal and the second output terminal; and
a switched-capacitor circuit-output unit receiving the first amplified output signal and the second amplified output signal to generate the common-mode feedback-input signal;
wherein the switched-capacitor circuit-input unit, the two switched-capacitor feedback-circuit unit, and the switched-capacitor circuit-output unit are further provided with a plurality of differential switches and a plurality of common-mode switches, wherein when the plurality of differential switches are turned on and the plurality of common-mode switches are turned off, the neural-signal amplifier is in a differential amplifying state; when the plurality of differential switches are turned off and the plurality of common-mode switches are turned on, the neural-signal amplifier is in a common-mode reconstructing state, wherein the neural-signal amplifier is controlled to switch between the differential amplifying state and the common-mode reconstructing state by operations the plurality of differential switches and the plurality of common-mode switches, so as to reconstruct a common-mode current to suppress DC current drift; wherein the neural-signal amplifier further comprises a switch-control unit electrically connected to the switched-capacitor circuit-input unit, the two switched-capacitor feedback-circuit units, and the switched-capacitor circuit-output unit, wherein the switch-control unit outputs a switch-control signal to control each of the differential switches and each of the common-mode switches, wherein when the switch-control signal is higher than a standard value, the plurality of differential switches are turned on and the plurality of common-mode switches are turned off; when the switch-control signal is lower than the standard value, the plurality of differential switches are turned off and the plurality of common-mode switches are turned on.

2. The neural-signal amplifier according to claim 1, wherein the switched-capacitor circuit-input unit comprises:
a first differential switch connected to a first bio-potential signal source which generates the first bio-potential signal;
a first common-mode switch connected between the first differential switch and a first capacitor, and the first capacitor connected to the first input terminal;
a second differential switch connected to a second bio-potential signal source which generates the second bio-potential signal;
a second common-mode switch connected between the second differential switch and a second capacitor, and the second capacitor connected to the second input terminal; and
a first reference voltage connected between the first common-mode switch and the second common-mode switch.

3. The neural-signal amplifier according to claim 2, wherein the switched-capacitor feedback-circuit unit comprises:
a third common-mode switch;

a fourth common-mode switch connected to a fifth bias source which supplies a fifth bias, and the fifth bias source further connected to the third common-mode switch;

a third differential switch connected to the fourth common-mode switch;

a third capacitor connected between the third common-mode switch and the fourth common-mode switch; and a low-pass capacitor connected between the third common-mode switch and the third differential switch;

wherein the third capacitor, the low-pass capacitor, and the third common-mode switch are connected to the first input terminal or the second input terminal, and the low-pass capacitor and the fourth common-mode switch are respectively connected to the first output terminal and the second output terminal.

4. The neural-signal amplifier according to claim 3, wherein the switched-capacitor circuit-output unit comprises:

a sixth common-mode switch connected to the first output terminal;

a seventh common-mode switch connected to the common-mode feedback-input terminal;

an eighth common-mode switch connected to the second output terminal;

a sixth differential switch having a terminal connected to the sixth common-mode switch, and another terminal connected to a fifth bias source which supplies a fifth bias;

a seventh differential switch having a terminal connected to the seventh common-mode switch, and another terminal connected to a first bias source which supplies a first bias;

an eighth differential switch having a terminal connected to the eighth common-mode switch, and another terminal connected to the fifth bias source which supplies the fifth bias;

a fifth capacitor having a terminal connected between the first output terminal and the seventh common-mode switch, and another terminal connected between the common-mode feedback-input terminal and the seventh differential switch;

a sixth capacitor having a terminal connected between the common-mode feedback-input terminal and the seventh common-mode switch, and another terminal connected between the second output terminal and the eighth common-mode switch;

a seventh capacitor having a terminal connected between the sixth common-mode switch and the eighth differential switch, and another terminal connected between the seventh common-mode switch and the seventh differential switch; and an eighth capacitor having a terminal connected between the seventh common-mode switch and the seventh differential switch, and another terminal connected between the eighth common-mode switch and the eighth differential switch.

5. The neural-signal amplifier according to claim 4, further comprising a bias-voltage generating unit, wherein the bias-voltage generating unit is electrically connected to the two switched-capacitor feedback-circuit units and the switched-capacitor circuit-output unit, and configured to generate the fifth bias and supply the fifth bias to the two switched-capacitor feedback-circuit units, and generates the fifth bias and the first bias and supplies the fifth bias and the first bias to the switched-capacitor circuit-output unit; wherein the bias-voltage generating unit is connected to a plurality of different bias sources.

6. The neural-signal amplifier according to claim 5, wherein the bias-voltage generating unit comprises a power-supply circuit formed by a Sooch Cascode current mirror.

7. The neural-signal amplifier according to claim 1, wherein the amplifier includes an amplifying circuit formed by a fully-differential folded common-source gate amplifier (FDFC Amp).

8. A multi-channel neural-signal amplifying system, comprising:

a plurality of neural-signal amplifier coupling units, wherein each of the neural-signal amplifier coupling units comprises a plurality of neural-signal amplifiers according to claim 1;

a plurality of analog-signal microprocessors, wherein each of the analog-signal microprocessors is coupled to one of the neural-signal amplifier coupling units; and a plurality of neural-signal sensing channels, and each of the neural-signal sensing channels connected to each of the neural-signal amplifiers.

* * * * *